US006685108B2

(12) United States Patent
Zhang

(10) Patent No.: US 6,685,108 B2
(45) Date of Patent: Feb. 3, 2004

(54) LIQUID SPRAYING APPARATUS

(76) Inventor: Zhi Xiong Zhang, Rm 8G, Blk. B, Tian Jian Ming Yuen, Xin Zhou Ru, Futian Dist, Shenzhen (CN)

( * ) Notice: Subject to any disclaimer, the term of this patent is extended or adjusted under 35 U.S.C. 154(b) by 0 days.

(21) Appl. No.: 10/143,917

(22) Filed: May 13, 2002

(65) Prior Publication Data

US 2003/0098370 A1 May 29, 2003

(30) Foreign Application Priority Data

Nov. 26, 2001 (CN) ............................................ 1258203

(51) Int. Cl.[7] .......................... B05B 9/04; A61M 11/06

(52) U.S. Cl. ....................................... 239/373; 239/338

(58) Field of Search ................................ 239/302, 346, 239/308, 338, 355, 373; 222/633

(56) References Cited

U.S. PATENT DOCUMENTS 339,206 A * 4/1886 Phelan ...................... 73/40.7
637,118 A * 11/1899 Hopper ....................... 366/333
814,820 A * 3/1906 Wood ......................... 239/362
2,560,093 A * 7/1951 Doble ........................ 222/633
5,785,245 A * 7/1998 Tedders et al. ................ 239/9

* cited by examiner

*Primary Examiner*—Michael J. Hayes
*Assistant Examiner*—Lina R Kontos
(74) *Attorney, Agent, or Firm*—Raymond Y. Chan; David & Raymond Patent Group

(57) ABSTRACT

This invention is related to sanitary apparatus, more particularly, it is involved with the liquid spraying apparatus (include spraying nozzle and its joint one-way valve; gasbag and its joint gas pipe; liquid container and the built-in water inlet pipe as well as the water inlet valve connected with the water inlet pipe.) used in the sanitary tools such as wringing mop, glass eraser, water broom and hair brush, etc. The nozzle, gasbag and liquid container shall be connected with a T-pipe. This newly invented liquid spraying device adopts liquid spraying principle based on pneumatic compression. The alkaline liquid and the cleaning water shall be sprayed out by pressing the gasbag. The device can be incorporated in various sanitary tools, with excellent reliability and convenient operation.

1 Claim, 2 Drawing Sheets

LIQUID SPRAYING APPARATUS

BACKGROUND OF THE PRESENT INVENTION

1. Field of Invention

The present invention relates to sanitary apparatus, and more particularly to a liquid spraying apparatus used for sanitary tools such as wringing mop, glass brush, water broom, and brush.

2. Description of Related Arts

At present, the conventional liquid spraying apparatus installed in sanitary tools is either artesian style or electric spraying style. However, the performance and reliability and reliability of such conventional apparatus are unstable.

Furthermore, it is very difficult for consumers to operate such conventional electric spraying style liquid spraying apparatus due to the complication of designs and assembly methods. Also, the application of such conventional liquid spraying apparatus is limited the hardly meets the market demand.

SUMMARY OF THE PRESENT INVENTION

The main objective of the present invention is to provide a liquid spraying apparatus, which is adapted for various types of sanitary tool for additional cleaning purposes.

Another objective of the present invention is to provide a liquid spraying apparatus which is simple in structure and highly reliable.

Another objective of the present invention is to provide a liquid spraying apparatus, which is convenient for use and effective for cleaning purposes.

Accordingly, in order to accomplish the above objectives, the present invention provides a liquid spraying apparatus, which comprises:

a spraying nozzle mounted on an end portion of a fronted part thereof;

a T-pipe connected with the spraying nozzle;

an inlet pipe with one end connected with the spraying nozzle and the T-pipe;

a one-way valve located at another end of the inlet pipe;

a gas pipe extending from the T-pipe;

a liquid container with at least one end mounted to a bottom portion of the T-pipe; and a gas pipe extended from the T-pipe to a gas bag which is a plastic hose linked up to the gas bag and down to one end of the T-pipe, wherein the T-pipe has an inlet connected with the inlet pipe of the liquid container and an outlet linked to the one-way valve.

DETAILED DESCRIPTION OF THE PREFERRED EMBODIMENT

Figure 1:
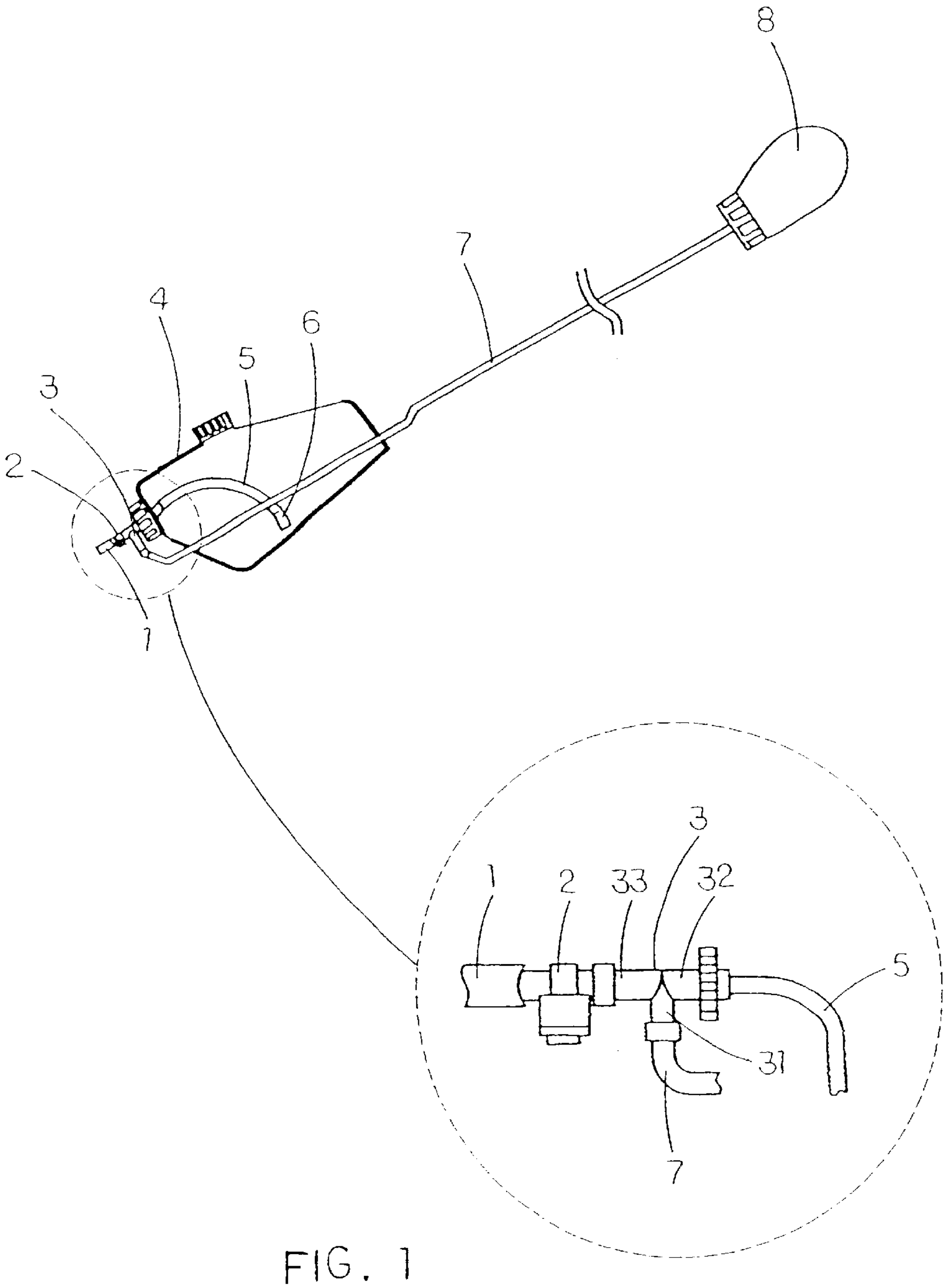
FIG. 1 is a structural schematic diagram of the liquid spraying apparatus according to a preferred embodiment of the present invention.

As illustrated in FIG. 1, a liquid spraying apparatus comprises a spraying nozzle 1, a one-way valve 2 connected to the spraying nozzle 1, a gas bag 8, an elongated gas pipe 7 connected to the one-way valve 2, a liquid container 4, an inlet pipe 5 disposed in the liquid container 4, and an inlet valve 6 which is connected with the inlet pipe 5. The spraying nozzle 1, the gas bag 8 and the liquid container 4 are linked up through a T-pipe 3.

The gas pipe, which is a flexible plastic hose, has one end linked up to the gas bag 8 and another end connected to a bottom end 31 of the T-pipe 3, according to the preferred embodiment of the liquid spraying apparatus.

One inlet end 32 of the T-pipe 3 links to the inlet pipe 5 inside the liquid container 4 and an outlet end 33 of the T-pipe 3 is connected with the one-way valve 2. The inlet pipe 5 connects to the inlet valve 6. The gas bag 8 is an elastic hollow body mad of rubber, according to the preferred embodiment.

Figure 2:
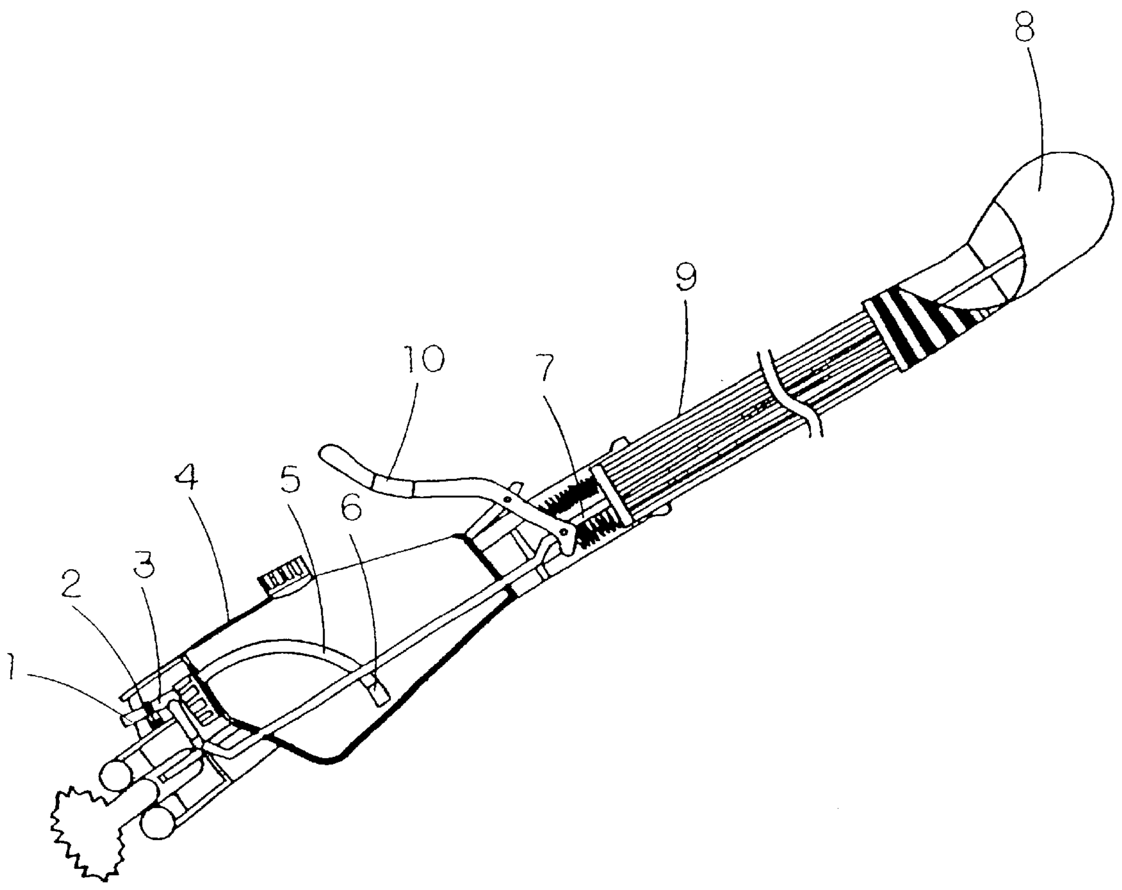
FIG. 2 is a sectional view of the liquid spraying apparatus installed in the sanitary tool according to the above preferred embodiment of the present invention.

The installation and operation of the liquid spraying apparatus is illustrated in FIG. 2. The liquid container 4 of the liquid spraying apparatus is affixed to a handle 9 while the gas pipe 7 penetrates through the handle 9, wherein the handle lever 10 and the handle 9 are arranged in a movable manner. The arrangement is operated by means of compressing and releasing the gas bag 8. When the gas bag 8 is compressed, the gas inside the gas bag 8 is compressed to pass through the T-pipe 3 via the gas pipe 7 to push the one-way valve 2 to open and to exhaust out from the spraying nozzle 1, wherein the gas also shuts up the inlet valve 6 via the inlet pipe 5 so as to provide an elasticity of the gas bag 8 to return to its original shape after the compression of the gas bag 8 is released. Thereafter, the alkaline liquid in the liquid container 4 is under atmospheric pressure and pushes the inlet valve 6 to open and enters the inlet pipe 5, wherein the one-way valve 2 is closed and the alkaline liquid is absorbed into the gas pipe 7 via the T-pipe 3. Accordingly, when the gas bag 8 is compressed again, the inlet valve 6 is closed and the alkaline liquid inside the gas pipe 7 and under the gas pressure is forced to spray out from the spraying nozzle.

After the compression to the gas bag 8 is released, the alkaline liquid is absorbed into the gas pipe 7 again. By repeatedly compressing and releasing of the gas bag 8, the alkaline liquid in the liquid container 4 will be absorbed and sprayed out through the spraying nozzle 1 via the inlet pipe 5, T-pipe 3, and the one-way valve 2. The alkaline liquid is sprayed out in a sector shape and evenly applied on the surface of an object.

The liquid spraying apparatus of the present invention adopts liquid spraying principle based on pneumatic compression. The alkaline liquid and the cleaning water shall be sprayed out by compressing the gas bag. Therefore, it is very convenient to use such liquid spraying apparatus for cleaning floors, doors and windows. The apparatus can also be incorporated in various sanitary tools, with simple and easy installation and low cost. For example, it can be installed in wringing mop, glass brush based on compressed spraying liquid and telescopic hair brush. Anyhow, it can be incorporated in all kinds of sanitary tool.

What is claimed is:

1. A liquid spraying apparatus for equipping with a sanitary tool, comprising:

a liquid container for receiving a liquid therein;

a gas bag, which is a hollow body made of elastic material for retaining gas therein, being capable of being compressed and retaining to an original shape thereof after a compression applied thereto is released;

a T-pipe having a bottom end, an inlet end and an outlet end;

a one-way valve connected with said outlet end of said T-pipe that only allows said liquid and gas to be emitted from said spraying nozzle;

a spraying nozzle, adapted for mounting to a front portion of said sanitary tool, being connected to said one-way valve;

an inlet pipe disposed in said liquid container having an upper end connected to said inlet end of said T-pipe;

an inlet valve connected to a lower end of said inlet pipe for disposing in said liquid of said liquid container; and an elongated gas pipe which has one end connected to said bottom end of said T-pipe and another end extended to linked up to said gas bag, wherein said gas pipe is adapted for extending through the sanitary tool for linking said spraying nozzle with said gas bag while said liquid spraying apparatus is installed to said sanitary tool, wherein when a first compression is applied to said gas bag, said gas inside said gas bag is compressed to pass through said T-pipe via said gas pipe to push said one-way valve to open and to exhaust out from said spraying nozzle, wherein said gas also shuts up said inlet valve via said inlet pipe so as to provide an elasticity of said gas bag to return to said original shape after said compression of said gas bag is released, thereafter said liquid in said liquid container is under atmospheric pressure and pushes said inlet valve to open and enters said inlet pipe, wherein said one-way valve is closed and said liquid is absorbed into said gas pipe via said T-pipe, accordingly when a second compression is applied to said gas bag again, said inlet valve is closed and said liquid inside said gas pipe and under a pressure of said gas is forced to spray out from said spraying nozzle, wherein after said second compression of said gas bag is released, said liquid is absorbed into said gas pipe again, therefore by repeatedly compressing and releasing of said gas bag, said liquid received in said liquid container is able to be absorbed and sprayed out through said spraying nozzle via said inlet pipe, said T-pipe and said one-way valve.

* * * * *